(12) United States Patent
Wynne et al.

(10) Patent No.: US 8,436,083 B2
(45) Date of Patent: May 7, 2013

(54) MULTIFUNCTIONAL SELF-DECONTAMINATING SURFACE COATING

(75) Inventors: James H Wynne, Alexandria, VA (US); Joanne M Jones-Meehan, Laurel, MD (US); Arthur W Snow, Alexandria, VA (US); Leonard J Buckley, Fairfax Station, VA (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 1522 days.

(21) Appl. No.: 11/969,954

(22) Filed: Jan. 7, 2008

(65) Prior Publication Data

US 2012/0172489 A1    Jul. 5, 2012

Related U.S. Application Data

(62) Division of application No. 11/183,305, filed on Jul. 14, 2005, now Pat. No. 7,339,015.

(60) Provisional application No. 60/622,715, filed on Oct. 28, 2004, provisional application No. 60/656,549, filed on Feb. 18, 2005.

(51) Int. Cl.
| | | |
|---|---|---|
| *A01N 25/00* | (2006.01) | |
| *A01N 33/18* | (2006.01) | |
| *A01N 33/24* | (2006.01) | |
| *A61K 9/14* | (2006.01) | |
| *A61K 31/045* | (2006.01) | |
| *B01F 17/00* | (2006.01) | |

(52) U.S. Cl.
USPC ........... 524/339; 424/405; 424/486; 424/487; 514/728

(58) Field of Classification Search ........... 523/122; 524/366, 375, 376, 560, 589, 590, 591, 599, 524/601, 612, 839, 840, 339; 424/405, 486, 424/487; 514/728; 526/313; 568/584, 608
See application file for complete search history.

(56) References Cited

U.S. PATENT DOCUMENTS

| | | | | |
|---|---|---|---|---|
| 3,563,924 | A | * | 2/1971 | Schwarz ................. 521/112 |
| 5,366,517 | A | * | 11/1994 | Cherpeck ................ 44/387 |
| 6,656,919 | B1 | * | 12/2003 | Baugh et al. ............ 514/46 |

* cited by examiner

*Primary Examiner* — Patrick Niland
(74) *Attorney, Agent, or Firm* — Any L. Ressing; Joseph T. Grunkemeyer

(57) ABSTRACT

A coating having an adhesive hydrophilic polymer and an amphiphilic additive. The amphiphilic additive has a hydrophilic chain, a biocidal functional group bonded to the hydrophilic chain, and a hydrophobic moiety bonded to the hydrophilic chain or to the biocidal functional group. A method of forming a biocidal surface by providing an article, and coating the article with the above coating. A compound having the formula:

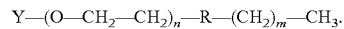

Y is $CH_3$ or H. R is

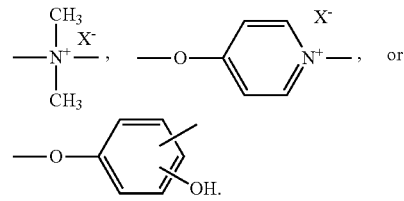

X is a halogen, and m and n are independently selected positive integers.

18 Claims, No Drawings

US 8,436,083 B2

MULTIFUNCTIONAL SELF-DECONTAMINATING SURFACE COATING

This application is a divisional application of U.S. patent application Ser. No. 11/183,305, which claims the benefit of U.S. Provisional Patent Application Nos. 60/622,715 filed on Oct. 28, 2004 and 60/656,549 filed on Feb. 18, 2005, all incorporated herein by reference.

BACKGROUND OF THE INVENTION

1. Field of the Invention

The invention is generally related to the fields of biocides and biocidal and/or sporicidal coatings.

2. Description of the Related Art

Decontamination and neutralization of surfaces from bacteria and spores is a complex process that involves multiple technologies and various approaches, depending on the nature and extent of contamination. There are a variety of commercially available biocides and antiviral coatings; however, there are very few that claim to be effective as sporicides. Moreover, many decontaminating agents and solvents used to prepare them must be mixed onsite and applied for effective use.

The ability to decontaminate chemically-resistant, coated painted surfaces inoculated with anthrax spores is extremely important. The anthrax spore is the most persistent of all biowarfare agents. To kill them, the most potent biocides/sporicides must be employed. Irradiation is frequently necessary and often ineffective due to the robustness of dormant or weaponized spores. Such spores may remain dormant for decades, yet are easily converted into the harmful or lethal vegetative form within minutes under ideal conditions.

Most conventional liquid sporicidal agents fall into three broad categories: halide releasing compounds (e.g., hypochlorites and iodophores), reactive oxygen releasing agents (e.g., peroxides and peracetic acid), and aldehydes (e.g., formalin and glutaraldehyde) (Russell, *Clin. Microbiology Rev.* 1990, 3, 99. All referenced publications and patent documents are incorporated herein by reference). Activity of all of these agents depend on destruction of fundamental metabolic processes and organic structures, thus making them extremely hazardous to personnel in many cases (Cross et al., *Appl. Environ. Microbiol.* 2003 69, 2245). Furthermore, many of these agents rely on the generation of very reactive chemical species and are thereby inherently unstable. Most commercial sterilants require activation prior to use and subsequently lose effectiveness within hours. The efficacy of some agents such as hypochlorites is rapidly attenuated by the presence of organic matter. Aldehydes are effective sporicides only at relatively high concentrations as liquids and require high relative humidity for effectiveness as vapors. Decontamination frequently utilizes extremely toxic gases such as ethylene oxide, chlorine dioxide, and methylene bromide (Whitney et al., *Emerging Infectious Diseases* 2003, 9, 623). Sporicidal efficacy of these gasses requires high relative humidity, and their use requires very careful attention to personnel safety. Anthrax spores pose a particularly difficult problem with respect to monitoring the success of the decontamination efforts. Previous literature reports that a variety of other functional groups have been effectively used as biocides; however, none cite the utility in surface overcoatings (Park et al., *Biomaterials* 1998, 19, 851).

Utility of germinants in solution have also been previously reported to aid in the conversion of spores into the vegetative cellular form; however, no mention of using this in decontamination was made (Cross et al.).

Bacteriocides have received much attention by way of industrial products, patent literature, as well as, peer-reviewed literature (Block, S. S. (ed.), 1991, *Disinfection, sterilization and preservation*, 4$^{th}$ edition. Lea & Febiger, Philadelphia, Pa.; Russell, A., D., W. B. Hugo and G. A. J. Ayliffe, 1992, *Principles and practice of disinfection, preservation and sterilization*. Blackwell Scientific Publications, London, U.K.). There have been many reports and patents dealing with the benefits of having surfaces capable of killing bacteria on contact (Ackart et al., *J. Biomed. Mater.* 1975, 9, 55-68; Endo et al., *Appl. Environ. Microbiol.* 1987, 53, 2050-2055; Gottenbos et al., *Biomaterials* 2002, 23, 1417-1423; Ottersbach et al., U.S. Pat. No. 5,967,714; Speir et al., *J. Colloid Interface Sci.* 1982, 89, 68-76; Tiller et al., *Biotechnol. Bioeng.* 2002, 79, 465-471; Tiller et al., *Proc. Natl. Acad. Sci.* 2002 98, 5981-5985; Bauth et al., U.S. Pat. No. 6,656,919). Despite the numerous reports, very few successful attempts to kill spores, more importantly the anthrax spore (*Bacillus anthracis*), have been made. A unique spray approach is reported; however, it requires treatment of a contaminated surface rather than serving as a preexisting coating (Bauth et al.). A common spore characteristic is the impervious outer coat. These outer coatings are very resistant to cold, heat, drought, harsh chemicals, mild radiation, many sporicides, and UV radiation (Mock et al., *Annu. Rev. Microbiol.* 2001, 55, 647-671).

The cell wall of a typical 1-2 μm vegetative bacterium is very complex, with multiple layers outside the cytoplasmic membrane. The structure of the cell wall consists of an outer glycocalyx capsule layer atop of an S-layer, peptidoglycan layer, and finally a plasmic membrane protecting the nucleus. In order to be effective, any biocide must be able to penetrate through this 40 nm outer wall consisting of layers such as glycocalyx, S-layer, peptidoglycan lipoteichoic acid layers to reach the vital parts in order to have an effect. Bactericidal functional groups are well known and are documented to target the cell membrane. Such products are currently commercially available as antiseptics, disinfectants, preservatives, sanitizers, water treatments, and swimming pool treatments. It has been reported that the bactericide mechanism starts with the adsorption onto a bacterial cell carboxylate surface followed by diffusion through the outer layers of the cell. The bonding to the cytoplasmic membrane and disruption of this membrane to result in the release of K$^+$ ions through leakage occurs, which results in degradation of the cell structure and release of cell contents, thus resulting in the death of the cell.

Quaternary ammonium, pyridinium, and phenolic compounds are known to possess biocidal activity and have been used in a variety of applications and numerous commercially available products. These compounds have not only found utility as biocides but also as phase transfer catalysts and mobility systems designed to aid in the drug delivery processes. They have also been reported to possess antiseptic properties.

SUMMARY OF THE INVENTION

The invention comprises a coating, comprising an adhesive hydrophilic polymer and an amphiphilic additive. The amphiphilic additive comprises a hydrophilic chain, a biocidal functional group bonded to the hydrophilic chain, and a hydrophobic moiety bonded to the hydrophilic chain or to the biocidal functional group.

The invention further comprises a method of forming a biocidal surface comprising providing an article, and coating the article with the above coating.

The invention further comprises a compound comprising the formula:

$$Y-(O-CH_2-CH_2)_n-R-(CH_2)_m-CH_3.$$

Y is $CH_3$ or H. R is selected from the group consisting of:

$$-\underset{CH_3}{\overset{CH_3}{\underset{|}{\overset{|}{N^+}}}}-\overset{X^-}{,} \quad -O-\underset{}{\overset{}{\text{C}_6\text{H}_4}}-\overset{X^-}{N^+}=, \quad \text{and}$$

$$-O-\text{C}_6\text{H}_3(\text{CH}_3)-\text{OH}.$$

X is a halogen, and m and n are independently selected positive integers.

DETAILED DESCRIPTION OF EXAMPLE EMBODIMENTS

In the following description, for purposes of explanation and not limitation, specific details are set forth in order to provide a thorough understanding of the present invention. However, it will be apparent to one skilled in the art that the present invention may be practiced in other embodiments that depart from these specific details. In other instances, detailed descriptions of well-known methods and devices are omitted so as to not obscure the description of the present invention with unnecessary detail.

The coating may be a multifunctional surface modifier. The coatings may have persistent bactericidal/bio-inhibitory activity coupled with a biocidal self-concentrating capability at polymer coating surfaces. The approach utilizes a hydrophobic/hydrophilic balance, such that the bactericidal functional group may self-orient toward the surface/air interface while retaining enough hydrophilic character to be compatible with the hydrophilic resin system and promote moisture retention. The approach makes use of a hierarchical four-component molecular system incorporated as an additive into selected polyurethane resin systems. The biocidal functional group is responsible for death of the cell. The hydrophobic moiety is responsible for orientation of the biocide functionality toward the surface of the over-coating. The hydrophilic chain functions to attract and retain moisture and for compatibility with the hydrophilic resin system. This may function in conjunction with the selected resin system to provide the needed moisture to germinate spores into the vegetative state. Finally, the adhesive polymer serves as a hydrophilic matrix for the dispersed or covalently bonded additives, a moisture reservoir and a conformal coating.

Although the spore form of *Bacillus anthracis* is extremely resistant to chemical disinfectants, the vegetative form of this bacterium is susceptible to conventional anti-bacterial compounds. The germination of bacterial spores is a studied phenomenon, and compounds (nutrients/germinants) that induce spore germination in liquid medium have been identified. These germinants are active at low concentrations, act very quickly, and may be very species specific. *Bacillus anthracis* germinants can be incorporated into the described coating systems, in such a way that adherent spores will be induced to germinate. Once the spores are converted into vegetative cells, they may be subsequently killed by the biocides present in the coating. This approach can eliminate the need to introduce highly toxic, short-lived, corrosive sporicides into the coating. Avoiding dependence on highly reactive short-lived chemicals can also dramatically increase the effective life of the top coating.

In one embodiment, the invention is a coating comprising an adhesive polymer and an amphiphilic additive as stated above. The coating may be applied to the surface of an article to give the surface biocidal properties.

The adhesive polymer facilitates binding to a substrate. Suitable adhesive hydrophilic polymers include, but are not limited to, polyurethanes, polyurethane hydrogels such as HYDROTHANE™ (CardioTech International, Inc), epoxies, polyesters, and polyacrylates. No particular minimum level of adhesiveness or hydrophilicity is required. The polymer need only adhere to a surface to be coated to a degree suitable for the manner in which the coated article is to be used. The polymer need only be hydrophilic enough to serve as a moisture reservoir for spore germination and to concentrate the amphiliphilic biocidal additive at the surface. The term "adhesive hydrophilic polymer" includes single polymers and combinations and mixtures of two or more polymers.

The hydrophilic chain of the amphiphilic additive is generally present in order to maintain the additive as part of the coating, through its attraction to the polymer, though it is not limited to such use. The hydrophilic chain may incorporate into the polymer by a variety of methods such as hydrogen bonding, covalent bonding, ionic coordination, or chain entanglement. The hydrophilic chain may also function as an attractive area for moisture absorption and as a promoter of germination. The hydrophilic chain may form a layer between the adhesive polymer and the biocidal group/hydrophobic moiety. The hydrophilic layer may include of several factors, such as physical or chemical bonding to an adhesive polymeric backbone, providing a source of moisture to promote the conversion from spore to vegetative bacterial cell, providing germinants to promote the conversion from spore to vegetative state, providing nutrients to promote the conversion from spore to vegetative state, attachment to a biocide functionality that will self-orientate towards the surface, and attachment to a biocide functionality that has the ability to kill the vegetative cell.

Suitable hydrophilic chains include, but are not limited to, oxyethylene oligomers and oxypropylene oligomers, including oligomers having 1, 2, 3, 4, 5, 6, 7, or 8 repeat units and/or terminating in methyl or hydroxyl. Oxyethylene is generally more hydrophilic than oxypropylene and may have a greater attraction to the polymer. The additive may contain a single hydrophilic chain or multiple hydrophilic chains that are the same or different, and the coating may contain two or more additives containing the same or different chains.

The hydrophobic moiety is generally present, though it is not limited to such use, in order to orient the additive such that the biocidal group is preferentially near or at the surface of the coating, thus allowing the biocidal component to be at the surface of the coating and not buried within the polymeric layer. No particular minimum level of hydrophobicity is required. Suitable hydrophobic moieties include, but are not limited to, alkyl groups, including linear alkyl groups having 2, 3, 4, 5, 6, 7, 8, 9, 10, 11, 12, 13, 14, 15, 16, 17, or 18 carbon atoms. The additive may contain a single moiety or multiple moieties that are the same or different, and the coating may contain two or more additives containing the same or different moieties.

The biocidal functional group is generally present in order to kill or be damaging to bacteria that come in contact with the coating, though it is not limited to such use. Suitable biocidal groups include, but are not limited to, quaternary ammonium salts, pyridinium salts, and phenols. The additive may contain a single biocidal group or multiple biocidal groups that are the same or different, and the coating may contain two or more additives containing the same or different biocidal groups. Suitable amounts of the amphiphilic additive or of the biocidal functional group include, but are not limited to, up to 5% or up to 1% by weight of the coating, such as 0.5% to 1%.

The amphiphilic additive may have the following structure:

$$Y-(O-CH_2-CH_2)_n-R-(CH_2)_m-CH_3.$$

Y is $CH_3$ or H. R is selected from the group consisting of:

X is a halogen, such as Cl, Br, or I; m is an integer from 1 to 17; and n is an integer from 1 to 8. In this class of compounds, $Y-(O-CH_2-CH_2)_n$ is the hydrophilic chain, $(CH_2)_m-CH_3$ is the hydrophobic moiety, and R is the biocidal group. The three R groups are, respectively, a quaternary ammonium salt, a pyridinium salt, and a phenol. The coating may comprise more than one of these compounds having more than one value for m, n, or both m and n, such that the coating as a whole has a non-integer average value for m and/or n.

In another embodiment, the coating comprises a germinating agent in addition to the amphiphilic additive. The germinant is generally present in order to stimulate conversion of a bacterium from spore form to vegetative form, though it is not limited to such use. An example of such a bacteria is *Bacillus anthracis*. The biocidal group may not have any effect on a spore, but once the germinating group causes the conversion, the biocidal group may act on the bacteria. Suitable germinating agents include, but are not limited to, L-alanine and L-methionine. More than one germinating agent may also be present in the coating. Suitable amounts of the germinating agent include, but are not limited to, up to 5% or up to 1% by weight of the coating.

The germinating coating may also comprise a nutrient. The nutrient is generally present to support development of the bacteria from the spore to the vegetative state. Suitable nutrients include, but are not limited to, Luria broth, and/or Yeast Extract and the compounds shown below. More than one nutrient may also be present in the coating. Suitable amounts of the nutrient include, but are not limited to, up to 5% or 1% by weight of the coating.

Features may include the ability for deposition as a polymeric thin film coating, controlled surface morphology/composition, promotion of spore germination, and bactericidal action. It involves the complex chemical and biological interactions acting across two dynamic interfaces or inter-phases between the bacteria/spore and the polymer coating. The concept for self-decontaminating surfaces is applicable to other bioagents besides *Bacillus anthracis* spores, such as *Yersinia pestis* (plaque) and *Francisella tularensis* (tularemia), as well as other pathogenic bacteria.

The coating or additive may be applied to a variety of surfaces to function as a self-decontaminator and function as a biocide, sporicide, and an antiviral agent. Several potential uses include children's toys, doorknobs, food preparation surfaces, air handling ducts, military equipment, military vehicles, public transportation surfaces, and other areas that are easily contaminated or areas that are in high risk of biological terrorist attacks. The coating may facilitate decontamination in enclosed or field areas.

Possible advantages may include eliminating the need for caustic chemicals, caustic sporicides, radiation, or precise environments to rid a surface of spores. This self-decontaminating coating or additive can allow for germination due to the presence of nutrients, germinants (including cogerminants), moisture, and biocidal functionality all incorporated at the surface of the coating and, thus, may be contacted by spores landing on the surface. The coating may be constantly active and may require no activation or special control of atmospheric conditions.

Another embodiment is compounds having the structure shown above, where m and n are independently selected positive integers. This embodiment includes mixtures of more than one such compounds having different values for m, n, or both m and n. Examples are shown below as well as example synthetic schemes. Suitable values for m are 1 to 17 and for n are 1 to 8, both including all numbers in between. This embodiment also includes mixtures of these compounds having more than one value for m, n, or both m and n.

Results indicate that the three classes of compounds have shown success. The biocidal functional groups and hydrophobic-hydrophilic substructures may each be varied independently. For each class of biocide, the minimum oxyethylene chain length that afforded the maximum effectiveness was incorporated into the selected resin systems. Depending upon the resin system selected, the minimum length was desirable in an attempt not to mask the hydrophobic substituent on the biocide, which dictated biocidal orientation within the coating. One of the many possible functional groups most suitable for incorporation into the resin systems described makes use of the acrylate moiety. The ability to retain the option to functionalize the hydrophilic chain with an acrylate may require modification to the synthetic approach (i.e., esterification) of the initial starting reagent within the reaction scheme.

The efficacy of these structures was evaluated in solution, prior to undertaking the additional synthetic steps that converted the molecules into the corresponding additive. These surfactant-like biocides have demonstrated effectiveness in killing bacteria not only in solution, but also in resin systems (i.e., urethanes, HYDROTHANE™). These systems were employed in screening diagnostics to obtain measures of water absorption and antimicrobial activity, which in turn may aid in the selection of the reported biocides. The lysing of the bacterial cells may result in the conversion of the halide salt into the corresponding hydroxide in some cases when pyridinium salts and/or ammonium salt species were employed.

A progression of results was demonstrated with Anthrax spores deposited on a 20% (w/w) hydrated HYDROTHANE™ resin system, which displayed no sign of conversion to the cellular form after weeks of incubation. This confirms that moisture alone on a surface or in the base resin system may not be sufficient to germinate Anthrax spores. When Anthrax spores were placed on the identical hydrated resin system, which included not only moisture but also a mixture of germinants, the spores became vegetative within hours. When the coating formulation included a biocide (i.e., quaternary ammonium biocide), very few spores remained and no growing bacteria remained on the surface. As a result of these initial evaluations, it was concluded that the spores germinated with the aid of both the moisture and germinant mixture within the polyurethane resin system. Subsequently, the bactericidal action of the ammonium salt effectively inactivated the resulting Anthrax cells, rendering a harmless surface. The proposed biocides are of a non-toxic character in contrast to many current heavy metal biocides.

Germinant/nutrient selection promoting vegetation of dormant anthrax spores is a very complex procedure because *Bacillus anthracis* does not rely on a single signal to promote spore germination. Receptor proteins on the spore's membrane bind to ring-shaped or aromatic structures on certain amino acids (building blocks of proteins) and purine ribonucleosides (building blocks of DNA and RNA). Small molecules or germinants have been reported to trigger spore germination for various bacterial spores (Clements et al., *J. Bacteriol.* 1998, 180, 6729; McCann et al., *Lett. Appl. Microbiol.* 1996, 23, 290; Rossignol et al., *J. Bacteriol.* 1979, 138, 431; Rossignol et al., *Biochem. Biophys. Res. Commun.* 1979, 89, 547; Vary et al., *J. Bacteriol.* 1968, 95, 1327; Mock et al., *Annu. Rev. Microbiol.* 2001, 55, 647; Hills, *Biochem. J.* 1949, 445, 363). Some reports specifically address Anthrax spores and cite L-alanine, purine, tryptophan, and tyrosine for *Bacillus anthracis* endospore germination, however; D-alanine inhibited germination (Titball et al., *J. Appl. Bacteriol.* 1987, 62, 269). Also, commercially formulated complex broths are used to culture various bacteria, and a combination of moisture and germinant are desirable for spore germination. The germination activity may be attributed to receptor proteins on the spore's membrane binding to heterocyclic aromatic structures and selected amino acids, resulting in conversion to the vegetative cellular form.

Spores have a redundant germination mechanism, which ensures they do not germinate until conditions are ideal. Small molecules or germinants have been found to trigger this process. Germinants that trigger the process include L-alanine in *Bacillus subtilis*, L-proline in *Bacillus megaterium*, and inosine in *Bacillus cereus* have been reported (Clements et al; McCann et al.; Rossignol et al., *J. Bacteriol.*; Rossigno et al., *Biochem. Biophys. Res. Commun*; Vary et al.). The germination of *Bacillus anthracis* endospores has been studied sporadically over the past sixty years. In 1949, Hills showed that germination was influenced by L-alanine, tyrosine, and adenosine (Hills *Biochem. J.* 1949, 445, 363-370). In 1987, Titball and Manchee showed L-alanine initiated *Bacillus anthracis* endospore germination, while D-alanine inhibited germination (Titball et al.).

A series of antimicrobial testing and results indicate success. A series of Gram-positive and Gram-negative bacteria were tested by four test methods (live/dead bacterial viability staining, disk diffusion test, tube dilution method with neutralization agent to quench residual biocide activity and coated glass slide). The following Gram-positive bacteria were used in the biocide tests: *Bacillus anthracis* Sterne strain, *Bacillus subtilis, Enterococcus faecalis, Staphylococcus aureus* and *Staphylococcus epidermidis*. The following Gram-negative bacteria were used in the biocide tests: *Escherichia coli, Klebsiella pneumoniae, Pseudomonas aeruginosa, Salmonella typhimurium, Enterobacter cloacae, Proteus vulgaris*, and *Serratia marcescens*. The prescreening of a series of model biocide compounds was very successful in killing vegetative bacterial cells for all functionalities of interest.

The approach of the present invention is designed to accelerate spore germination by the addition of known cogerminants for *Bacillus anthracis* such as L-alanine+L-amino acids (trp, tyr, pro, his); inosine with aromatic and non-aromatic L-amino acids (trp, tyr, phe, his, pro, phe, ser, val, ser) (Ireland et al., *Medicine at Michigan* 2002 4:12; Ireland et al., *J. Bacteriol.* 2002 184:1296-1303). In the present invention, the following cogerminants may be added to the coating system: poly L-alanine, poly-L-tryptophan (various molecular weights), poly-L-tyrosine (various molecular weights), poly-L-amino acid peptides, inosine, ATP, etc. Addition of pigments, fillers, polyester, amides, poly L-alanine, Yeast Extract, Luria Broth, etc. can act as nutrients in the presence of moisture.

Identification of key components/compounds that are strong promoters of spore germination is necessary. Results employing commercial mixtures of germinants (e.g., Luria Broth (LB)), a mixture consisting of yeast extract, tryptone and sodium chloride has shown success, when employed in 0.1-20% (w/w) concentrations within the hydrophilic resin system. Yeast extract with various L-amino acids (i.e., L-alanine, L-methionine, etc.) has shown success as germinants for *Bacillus anthracis* spores.

Screening may be conducted employing a variety of amino acids, heterocyclics, and components of commercial growth media. The rapid screening and down selection from an extensive list of the germinants may allow for rapid optimization. The germinants may be ranked and down-selected according to time dependence for germination. The more effective germinant candidates have demonstrated the minimum effective concentration required for the desired response within the resin system. After selection in the test resin system, the germinants were then optimized for the final selected resin coating system.

Having described the invention, the following examples are given to illustrate specific applications of the invention. These specific examples are not intended to limit the scope of the invention described in this application.

Example 1

General procedure for preparation of methoxy terminated quaternary ammonium salts—In a 20 mL round bottomed flask equipped with reflux condenser and a positive flow of nitrogen were placed a tertiary amine (6.36 mmol), a bromoethyleneglycol monomethyl ether (6.36 mmol), and absolute ethanol (17.49 mmol). The solution was heated in an 83° C. oil bath for 24 hr. The resulting solution was allowed to slowly cool to RT and concentrated under reduced pressure. The resulting thick yellow oil was titrated with petroleum ether (2×3 mL), and placed under vacuum to remove trace solvent. The resulting product was dissolved in 2 mL of EtOH with vigorous stirring and then cooled to −30° C. to result in crystallization of the desired product. A second crop of equal purity may be recovered by recrystallization of the mother liquor.

Example 2

Characterization of methoxy terminated quaternary ammonium salts—Hexyl-[2-(2-methoxy-ethoxy)-ethyl]-dimethyl-ammonium bromide: FTIR: 3013, 2954, 2921, 2878, 1463, 1253, 1194 $cm^{-1}$. $^1$H NMR ($CDCl_3$): 3.99-3.92 (dd, 4H), 3.72-3.58 (m, 4H), 3.54-3.51 (m, 2H), 3.42 (s, 6H), 3.36 (s, 3H), 1.78-1.74 (m, 2H), 1.34-1.31 (m, 6H), 0.90 (t, J=7, 3H) δ. $^{13}$C NMR ($CDCl_3$): 71.4, 70.3, 65.7, 64.9, 62.8, 58.8, 58.0, 51.8, 31.1, 25.7, 22.7, 22.3, 13.7 δ. Anal. Calcd for $C_{13}H_{30}BrNO_2$: C, 50.00; H, 9.68; N, 4.49. Found: C, 49.87; H, 9.71; N, 4.49.

Hexyl-(2-methoxy-ethyl)-dimethyl-ammonium bromide—FTIR: 3005, 2949, 2922, 2854, 2811, 1467, 1408, 1380, 1265, 1118, 1078, 1031, 729 $cm^{-1}$. $^1$H NMR ($CDCl_3$): 3.95-3.87 (dd, 4H), 3.61 (t, J=8, 2H), 3.43 (s, 6H), 3.40 (s, 3H), 1.79-1.61 (m, 2H), 1.37-1.31 (m, 6H), 0.89 δ (t, J=7, 3H). $^{13}$C NMR ($CDCl_3$): 65.9, 65.2, 62.5, 58.6, 51.3, 30.6, 25.3, 22.2, 21.8, 17.9, 13.4 δ. Anal. Calcd for $C_{11}H_{26}BrNO$: C, 49.25; H, 9.77; N, 5.22. Found: C, 49.21; H, 9.75; N, 5.25.

(2-Methoxy-ethyl)-dimethyl-octyl-ammonium bromide—FTIR: 3005, 2949, 2921, 2850, 2810, 1467, 1122, 1031, 722 $cm^{-1}$. $^1$H NMR ($CDCl_3$): 3.94 (d, J=5, 2H), 3.87 (d, J=5, 2H), 3.87-3.62 (m, 2H), 3.43 (s, 6H), 3.39 (s, 3H), 1.34-1.24 (m, 10H), 1.78-1.72 (m, 2H), 0.88 (t, J=7, 3H) δ. $^{13}$C NMR ($CDCl_3$): δ6.4, 65.9, 63.0, 59.1, 51.8, 31.6, 29.0, 28.9, 26.2, 22.8, 22.5, 14.0 δ. Anal. Calcd for $C_{13}H_{30}BrNO$: C, 52.70; H, 10.21; N, 4.73. Found: C, 52.32; H, 10.14; N, 4.77.

[2-(2-Methoxy-ethoxy)-ethyl]-dimethyl-octyl-ammonium bromide—FTIR: 3009, 2954, 2922, 2851, 2815, 1471, 1360, 1134, 1099, 1071, 1015, 976, 841 $cm^{-1}$. $^1$H NMR ($CDCl_3$): 3.95-3.91 (m, 4H), 3.72-3.52 (m, 6H), 3.40 (s, 3H), 3.35 (s, 6H), 1.78-1.72 (m, 2H), 1.34-1.21 (m, 10H), 0.90 (t, ∂=7, 3H) δ. $^{13}$C NMR ($CDCl_3$): 71.4, 70.3, 65.8, 64.9, 62.8, 58.8, 58.0, 51.8, 31.5, 28.9, 26.1, 22.8, 22.4, 18.3, 13.9 δ. Anal. Calcd for $C_{15}H_{34}BrNO_2$: C, 52.94; H, 10.07; N, 4.12. Found: C, 52.71; H, 10.27; N, 4.05.

Hexyl-(2-(2-(2-methoxy-ethoxy)-ethoxy)-ethyl)dimethylammonium bromide: FTIR: 3005, 2954, 2922, 2858, 1633, 1467, 1352, 1277, 1245, 1201, 1110, 964 $cm^{-1}$. $^1$H NMR ($CDCl_3$): 4.08-3.94 (m, 4H), 3.82-3.47 (m, 8H), 3.43 (s, 6H), 3.37 (s, 3H), 1.77 (t, J=5, 2H), 1.35-1.21 (m, 8H), 0.89 δ (t, J=6, 3H). $^{13}$C NMR ($CDCl_3$): 71.7, 71.0, 70.4, 70.2, 69.9, 65.7, 64.8, 58.8, 51.7, 30.7, 25.8, 22.7, 18.3, 13.8 δ. Anal. Calcd for $C_{15}H_{34}BrNO_3$: C, 50.56; H, 9.62; N, 3.93. Found: C, 50.75; H, 9.91; N, 3.65.

Hexyl-(2-(2-(2-(2-methoxy-ethoxy)-ethoxy)-ethoxy)-ethyl)dimethylammonium bromide: FTIR: 3005, 2950, 2926, 2870, 1467, 1348, 1249, 1118, 964 $cm^{-1}$. $^1$H NMR ($CDCl_3$): 4.06-3.92 (m, 6H), 3.73-3.54 (m, 8H), 3.63 (s, 6H), 3.47-3.37 (m, 2H), 3.37 (s, 3H), 1.76 (t, J=6, 2H), 1.38-1.30 (m, 8H), 0.90 δ (t, J=6, 3H). $^{13}$C NMR ($CDCl_3$): 71.8, 70.5, 70.4, 70.3, 70.2, 70.1, 65.9, 65.0, 63.0, 58.9, 51.8, 31.2, 25.8, 22.8, 22.7, 22.3, 13.8 δ. Anal. Calcd for $C_{17}H_{38}BrNO_4$: C, 51.00; H, 9.57; N, 3.50. Found: C, 50.59; H, 9.52; N, 3.87.

(2-(2-(2-Methoxy-ethoxy)-ethoxy)-ethyl)dimethyloctylammonium bromide: FTIR: 3009, 2957, 2924, 2856, 1627, 1465, 1356, 1275, 1243, 1198, 1125, 968 $cm^{-1}$. $^1$H NMR ($CDCl_3$): 4.12-3.87 (m, 4H), 3.63-3.47 (m, 8H), 3.42 (s, 6H), 3.29 (s, 3H), 1.76 (t, J=5, 2H), 1.26-1.01 (m, 12H), 0.88 δ (t, J=6, 3H). $^{13}$C NMR ($CDCl_3$): 71.7, 70.9, 70.4, 70.3, 70.1, 69.9, 66.0, 58.9, 51.8, 31.5, 29.0, 28.95, 26.2, 22.8, 22.5, 13.9 δ. Anal. Calcd for $C_{17}H_{38}BrNO_3$: C, 53.12; H, 9.96; N, 3.64. Found: C, 52.89; H, 9.77; N, 3.46.

(2-(2-(2-(2-Methoxy-ethoxy)-ethoxy)-ethoxy)-ethyl)dimethyloctylammonium bromide: FTIR: 3005, 2926, 2854, 1467, 1344, 1292, 1253, 1118, 975, 928 $cm^1$. $^1$H NMR ($CDCl_3$): 4.06-3.93 (m, 6H), 3.82-3.68 (m, 8H), 3.63 (s, 6H), 3.39-3.38 (m, 2H), 3.45 (s, 3H), 1.76 (t, J=6, 2H), 1.35-1.21 (m, 12H), 0.88 (t, J=6, 3H) δ. $^{13}$C NMR ($CDCl_3$): 71.7, 71.0, 70.4, 70.3, 70.2, 65.8, 64.9, 62.8, 58.2, 51.7, 31.5, 30.6, 29.0, 28.9, 26.1, 22.7, 22.7, 18.3, 13.9 δ. Anal. Calcd for $C_{19}H_{42}BrNO_4$: C, 53.26; H, 9.88; N, 3.27. Found: C, 52.89; H, 9.65; N, 3.24.

Example 3

General procedure for preparation of hydroxyl terminated quaternary ammonium salts—In a 15 mL round bottomed flask equipped with condenser, magnetic stir bar, and positive flow of nitrogen were placed amine (6.36 mmol), 2-(2-chloroethyl)ethanol (0.79 g, 6.36 mmol), and 0.80 g of absolute EtOH (17.49 mmol). The resulting solution was allowed to stir in a 90° C. oil bath for 24 hr, after which time the solution was allowed to cool to RT. The solution was concentrated under reduced pressure and tritrated with petroleum ether (3×2 mL). The resulting viscous oil was dissolved in 5 mL of EtOH and passed through a 3 cm plug of Sephadex G-25 resin with an additional 50 mL EtOH wash. The solution was concentrated to afford the desired product.

Example 4

Preparation of [2-(2-hydroxy-ethoxy)-ethyl]-dimethyl-octyl-ammonium chloride—Dimethyl-octyl-amine (1.00 g, 6.36 mmol) was condensed with 2-(2-chloro-ethoxy)-ethanol (1.19 g, 9.54 mmol) in a 25 mL round bottomed flask equipped with magnetic stir bar and allowed to heat in a 120° C. oil bath for 6 hrs. The solution was slowly cooled to room temperature, which resulted in semisolid formation. The resulting product was placed on vacuum at 1 mmHg and heated at 60° C. for 4 hrs to remove unreacted amine and starting material.

Example 5

Alternative preparation of [2-(2-hydroxy-ethoxy)-ethyl]-dimethyl-octyl-ammonium chloride—Into a 15 mL round-bottomed flask with positive flow of nitrogen were placed N,N-dimethyloctylamine (6.36 mmol), 3 mL THF, and 2-(2-chloro-ethoxy)-ethanol (6.36 mmol). The resulting solution was allowed to reflux for 12 hr. Upon cooling to room temperature, the solution was concentrated under reduced pressure and dried under reduced pressure at 100° C. to rid the product mixture from subsequent residual starting material.

Example 6

Characterization of hydroxyl terminated quaternary ammonium salts—Octyl-(2-(2-hydroxy-ethoxy)-ethyl)dimethylammonium chloride: FTIR: 3279, 3009, 2954, 2921, 2858, 1467, 1364, 1126, 1071, 971, 892 cm$^{-1}$. $^1$H NMR (CDCl$_3$): 4.05 (d, J=6, 2H), 3.86 (t, J=6, 2H), 3.80-3.73 (m, 2H), 3.69-3.54 (m, 4H), 3.41 (s, 6H), 2.67 (bs, 1-OH), 1.34-1.27 (m, 12H), 0.885 (t, J=6, 3H). $^{13}$C NMR (CDCl$_3$): 72.9, 72.3, 71.0, 64.8, 61.5, 61.1, 51.8, 42.9, 31.6, 28.9, 26.2, 22.8, 22.5, 14.0 δ. Anal. Calcd for C$_{14}$H$_{32}$ClNO$_2$: C, 59.66; H, 11.44; N, 4.97. Found: C, 59.81; H, 11.52; N, 4.59.

Hexyl-(2-(2-hydroxy-ethoxy)-ethyl)dimethylammonium chloride: FTIR: 3229, 3016, 2955, 2928, 2861, 1467, 1359, 1123, 1069, 965 cm$^1$. $^1$H NMR (CDCl$_3$): 3.87 (d, J=5, 2H), 3.69 (t, J=5, 2H), 3.63-3.37 (m, 4H), 3.23 (s, 6H), 2.65 (bs, 1OH), 1.65-1.50 (m, 2H), 1.27-1.11 (m, 8H), 0.72 δ (t, J=7, 3H). $^{13}$C NMR (CDCl$_3$): 73.0, 66.0, 63.5, 61.2, 51.8, 31.2, 25.9, 22.8, 22.4, 18.4, 13.8 δ. Anal. Calcd for C$_{12}$H$_{28}$ClNO$_2$: C, 56.79; H, 11.12; N, 5.52. Found: C, 56.82; H, 11.05; N, 5.74.

Example 7

General procedure for preparation of phenols—In a 25 mL round bottomed flask equipped with magnetic stir bar, Dean-Stark trap and condenser were placed 4-Hexyl-benzene-1,3-diol (0.59 g, 6.25 mmol), an ethyleneoxide monomethylether (6.25 mmol), p-toluenesulfonic acid (0.01 g, 0.008 mmol), and 20 mL of toluene. An additional 7 mL of toluene was placed in the Dean-Stark trap to prevent taking the pot volume too low. The solution was allowed to reflux vigorously for 24 hours in an oil bath. The resulting solution was allowed to cool to room temperature, concentrated using the rotary evaporator. The resulting oil was eluted through a silica gel column employing a Hexane/EtOAc (1:1) solvent system. The desired product eluted in the first fraction.

Example 8

Preparation of 2-Hexyl-4-(2-{2-[2-(2-methoxy-ethoxy)-ethoxy]-ethoxy}-ethoxy)-phenol—To a solution of toluene-4-sulfonic acid 2-{2-[2-(2-methoxy-ethoxy)-ethoxy]-ethoxy}-ethyl ester (1.87 g, 5.15 mmol) dissolved in 50 mL tetrahydrofuran in a 100 mL round bottomed flask equipped with nitrogen inlet, condenser, and a stir bar was added dropwise 2-hexyl-benzene-1,4-diol (1.00 g, 5.15 mmol). The resulting solution was heated in an 80° C. oil bath for 12 hours with rigorous stirring. After such time, it was allowed to slowly cool to room temperature and was concentrated utilizing a rotary evaporator. The resulting product was washed with deionized water (3×5 mL) to rid the mixture of any residual by-product and then placed on the vacuum line for 4 hours. The desired product, 2-hexyl-4-(2-{2-[2-(2-methoxy-ethoxy)-ethoxy]-ethoxy}-ethoxy)-phenol, was afforded in a 61% yield (1.22 g, 3.16 mmol).

Example 9

Characterization of phenols-2-Hexyl-5-(2-methoxy-ethoxy)-phenol: FTIR: 3362, 2950, 2930, 2858, 1606, 1519, 1463, 1376, 1297, 1221, 1162, 1114, 1055, 972 cm$^{-1}$. $^1$H NMR (CDCl$_3$): 6.91 (d, J=9, 1H), 6.34 (d, J=2, 1H), 5.76 (d, J=5, 2H), 3.54 (d, J=5, 2H), 3.37 (s, 3H), 2.48 (t, J=8, 2H), 1.55-1.50 (m, 2H), 1.34-1.25 (m, 6H), 0.87 δ (t, J=7, 3H). $^{13}$C NMR (CDCl$_3$): 154.3, 154.2, 130.7, 121.3, 107.5, 102.9, 73.4, 61.5, 58.7, 31.7, 29.2, 29.1, 22.6, 14.1 δ.

2-Hexyl-5-[2-(2-methoxy-ethoxy)-ethoxy]-phenol: FTIR: 3346, 2961, 2922, 2858, 1622, 1519, 1459, 1376, 1301, 1225, 1166, 1118, 968 cm$^{-1}$. $^1$H NMR (CDCl$_3$): 6.92 (d, J=9, 1H), 6.36 (d, J=2, 1H), 6.32 (d, J=6, 1H), 5.37 (bs, 10H), 3.78 (t, J=6, 2H), 3.66 (t, J=5, 2H), 3.63-3.59 (m, 4H), 3.42 (s, 3H), 2.50 (t, J=6, 2H), 1.55-1.51 δ (m, 2H). $^{13}$C NMR (CDCl$_3$): 154.6, 154.4, 130.6, 120.9, 107.4, 102.8, 72.2, 71.9, 69.9, 61.8, 58.9, 31.7, 30.0, 29.2, 29.1, 22.6, 14.1 δ.

2-Hexyl-5-{2-[2-(2-methoxy-ethoxy)-ethoxy]-ethoxy}-phenol (3c): FTIR: 3345, 2950, 2913, 2851, 1626, 1601, 1519, 1459, 1380, 1348, 1301, 1217, 976 cm$^{-1}$. $^1$H NMR (CDCl$_3$): 6.91 (d, J=9, 1H), 6.41 (d, J=2, 1H), 6.33 (d, J=6, 1H), 3.77-3.73 (m, 2H), 3.70-3.56 (m, 10H), 3.38 (s, 3H), 2.50 (t, J=6, 2H), 1.55-1.49 (m, 2H), 1.33-1.27 (m, 6H), 0.87 δ (t, J=6, 3H). $^{13}$C NMR (CDCl$_3$): 155.0, 154.7, 130.5, 120.7, 106.9, 102.6, 72.4, 71.7, 70.5, 70.3, 70.2, 61.6, 58.9, 31.8, 30.0, 29.3, 29.2, 22.6, 14.1 δ.

2-Hexyl-5-(2-{2-[2-(2-methoxy-ethoxy)-ethoxy]-ethoxy}-ethoxy)-phenol: FTIR: 3342, 2930, 2858, 1618, 1606, 1523, 1459, 1344, 1301, 1253, 1198, 1094, 980 cm$^{-1}$. $^1$H NMR (CDCl$_3$): 6.91 (d, J=9, 1H), 6.41 (d, J=2, 1H), 6.33 (d, J=6, 1H), 3.75 (t, J=6, 2H), 3.68-3.55 (m, 14H), 3.37 (s, 3H), 2.50 (t, J=9, 2H), 1.55-1.52 (m, 2H), 1.33-1.24 (m, 6H), 0.87 δ (t, J=6, 3H). $^{13}$C NMR (CDCl$_3$): 155.0, 154.7, 130.5, 120.7, 106.9, 102.7, 72.4, 71.8, 70.5 (overlapping peak), 70.4, 70.3, 70.1, 61.7, 58.8, 31.8, 30.1, 29.3, 29.2, 22.6, 14.1 δ.

Example 10

Preparation of 1-hexyl-4-(2-{2-[2-(2-methoxy-ethoxy)-ethoxy]ethoxy}-ethoxy)-pyridinium bromide—Pyridin-4-ol (1.50 g, 15.77 mmol) and toluene-4-sulfonic acid 2-{2-[2-(2-methoxy-ethoxy)-ethoxy]-ethoxy}-ethyl ester (5.62 g, 19.71 mmol) were combined in a 50 mL round bottomed flask equipped with condenser, magnetic stir bar, and a positive flow of nitrogen. The solution was heated in a 100° C. oil bath for 24 hrs. The solution was then cooled and placed on a vacuum line at 1 mmHg and heated at 80° C. for 6 hrs to removed residual starting materials. The by-product was removed via washing with deionized water (3×15 mL) to afford 4-(2-{2-[2-(2-methoxy-ethoxy)-ethoxy]-ethoxy}-ethoxy)-pyridine. The product may be subsequently purified employing column chromatography techniques at this point or may proceed directly to the addition of 1-bromohexane (3.90 g, 23.66 mmol) in 25 mL tetrahydrofuran. Stirring the resulting reaction mixture at 50° C. for 24 hrs resulted in the desired product, 1-hexyl-4-(2-{2-[2-(2-methoxy-ethoxy)-ethoxy]-ethoxy}-ethoxy)-pyridinium bromide in a 38% yield (2.70 g, 5.99 mmol).

Example 11

Preparation of 1-hexyl-4-{2-[2-(2-methoxy-ethoxy)-ethoxy]-ethoxy}-pyridinium bromide—Into a 25 mL round bottomed flask with positive flow of nitrogen, were placed 4-hydroxy pyridine (2.14 mmol), toluene-4-sulfonic acid 2-[2-(2-methoxy-ethoxy)-ethoxy]-ethyl ester (2.36 mmol), and 15 mL THF. The resulting solution was allowed to reflux for 24 hr, slowly allowed to cool to room temperature and then treated with 1-chlorohexane (2.36 mmol), prior to bringing the solution to reflux once again for 6 hr. The reaction mixture was concentrated under reduced pressure and titrated with hexanes.

Example 12

Antimicrobial testing—Live/dead bacterial viability staining was employed. This is a two-color fluorescence assay of bacterial viability, which provided results in minutes. This is a quantitatively method used to distinguish live and dead bacteria in minutes even in a mixed population of bacterial types. SYTO-9 green fluorescent nucleic acid stain bacteria with intact membranes stain fluorescent green; excitation/emission maxima are 490/635 nm. Disk diffusion test, tube dilution method with neutralizing agent to quench residual activity (results shown in Table 1) and coated glass slides were the primary methods of evaluating model compounds.

A variety of gram-positive and gram-negative bacteria were tested. A few of the Gram+utilized included: *Bacillus anthracis* Sterne strain, *Bacillus subtilis*, *Enterococcus faecalis*, and *Staphylococcus aureus*. Gram-utilized included: *Escherichia coli*, *Klebsiella pneumoniae*, *Pseudomonas aeguginosa*, *Salmonella typhimurium*, *Enterobacter cloacae*, *Proteus vulgaris*, and *Serratita marcescens*.

TABLE 1

| Biocide | S. aureus | E. Coli | B. anthracis S. S. |
|---|---|---|---|
| Pyridinium | $10^6$ | $10^7$ | $10^6$ |

TABLE 1-continued

| Biocide | S. aureus | E. Coli | B. anthracis S. S. |
|---|---|---|---|
| Phenol | NG | NG | NG |
| QUAT $C_6$ | $10^5$ | $10^7$ | $10^7$ |
| QUAT $C_4$ | $10^3$ | NG | $10^2$ |
| Imideoxime | $10^6$ | $10^7$ | $10^6$ |

NG—no growth;
starting cfu/mL: *S. aureus*, $5.46 \times 10^7$; *E. coli*, $4.76 \times 10^7$ and *B. anthracis* Sterne, $4.09 \times 10^7$.

Quaternary ammonium biocides were subjected to minimum inhibitory concentration (MIC) studies for effectiveness comparisons (Table 2). Two Gram-positive bacteria (*S. aureus* and *B. anthracis* Sterne strain), were employed along with two Gram-negative bacteria (*Escherichia coli* and *Salmonella typhimurium*). In all cases, those biocides possessing the octyl alkyl functionality were more effective antimicrobials than the corresponding analogs possessing the hexyl group. The biocides possessing the hexyl moiety appeared to be more effective against Gram-negative versus Gram-positive bacteria; while those possessing the octyl moiety showed a lower MIC for Gram-positive bacteria versus Gram-negative bacteria.

The comparison study of hydroxyl-terminated biocides (entries 9 and 10) with the corresponding methoxy terminated analogs (6 and 2) respectively, showed similar responses. The hydroxyl terminated octyl derivative (9) was more effective than the corresponding hexyl analog (10) for three of the bacteria tested. While identical MIC results were obtained for *E. coli.*, with hydroxyl or methoxy terminated analogs. The hydroxyl terminated hexyl (9) was more effective against Gram-positive versus Gram-negative bacteria. The hydroxyl terminated octyl derivative did not performed well with any of the bacteria tested.

When the alkyl functionality was held constant, the following observations were noted when the length of the hydrophilic oxyethylene terminus was varied. In the case of the octyl functionality, in general the oxyethylene unit of 1 or 4 (5 and 8) was more effective as an antimicrobial than those possessing 2 or 3 units (6 and 7). Similar results were observed for the hexyl analog, with lesser variances. It was noted that the additional oxyethylene unit assisted in solubilization, but no noticeable increase in antimicrobial activity was observed. It may be possible that aggregation into micelles could be affecting antimicrobial activity by hindering the biocidal functional groups as seen in MIC for entries 2, 3, 6, and 7. Shorter linkages resulted in an observed increased neutralization. The actual correlation of kill with oxyethylene chain length remains unknown and is the subject of ongoing studies in our laboratory. No observable difference was noted between the two anions tested.

From results of this study, the antimicrobial activity can be listed as entry 5>8>7. These three biocides were effective against the Gram-positive and Gram-negative bacteria tested. It was concluded that the octyl chain performed better than the corresponding hexyl derivatives.

| Entry | Y | m | n | X | S. aureus (Gram+) | B. anthracis (Gram+) | E. coli (Gram−) | S. typhimurium (Gram−) |
|---|---|---|---|---|---|---|---|---|
| 1 | $CH_3$ | 5 | 1 | Br | 2.5 | 5 | 2.5 | 2.5 |
| 2 | $CH_3$ | 5 | 2 | Br | >5 | >5 | 2.5 | >5 |
| 3 | $CH_3$ | 5 | 3 | Cl | >5 | 2.5 | 2.5 | >5 |
| 4 | $CH_3$ | 5 | 4 | Cl | 2.5 | 5 | 2.5 | 5 |
| 5 | $CH_3$ | 7 | 1 | Cl | 0.18 | <0.3125 | 0.625 | 2.5 |
| 6 | $CH_3$ | 7 | 2 | Cl | 0.31 | 1.25 | 2.5 | 5 |
| 7 | $CH_3$ | 7 | 3 | Cl | 0.5 | 0.625 | 2.5 | 2.5 |

-continued

| Entry | Y | m | n | X | S. aureus (Gram+) | B. anthracis (Gram+) | E. coli (Gram−) | S. typhimurium (Gram−) |
|---|---|---|---|---|---|---|---|---|
| 8 | CH₃ | 7 | 4 | Cl | 0.8 | 0.3125 | 1.25 | 2.5 |
| 9 | H | 7 | 2 | Cl | 1.25 | 1.25 | 5 | 5 |
| 10 | H | 7 | 2 | Cl | >5 | >5 | 5 | >5 |

Obviously, many modifications and variations of the present invention are possible in light of the above teachings. It is therefore to be understood that the claimed invention may be practiced otherwise than as specifically described. Any reference to claim elements in the singular, e.g., using the articles "a," "an," "the," or "said" is not construed as limiting the element to the singular.

What is claimed is:

1. A coating, comprising:
an adhesive hydrophilic polymer; and
an amphiphilic additive, wherein the amphiphilic additive has the formula:

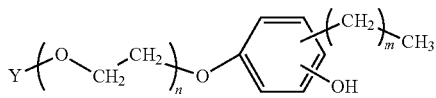

wherein Y is CH₃ or H; and
wherein m and n are independently selected positive integers.

2. The coating of claim 1,
wherein m is an integer from 1 to 17; and
wherein n is an integer from 1 to 8.

3. The coating of claim 1, wherein the adhesive hydrophilic polymer is selected from the group consisting of polyurethanes, polyurethane hydrogels, epoxies, polyesters, and polyacrylates.

4. The coating of claim 1, wherein the coating comprises more than one of the compounds;
wherein the compounds have more than one value for m, n, or both m and n.

5. The coating of claim 1, wherein the coating further comprises a germinating agent.

6. The coating of claim 5, wherein the germinating agent is selected from the group consisting of L-alanine and L-methionine.

7. The coating of claim 5, wherein the coating further comprises a nutrient.

8. The coating of claim 7, wherein the nutrient is Luria broth.

9. A compound comprising the formula:

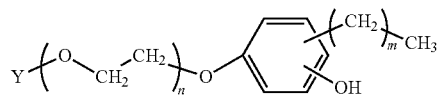

wherein Y is CH₃ or H; and
wherein m is a positive integer; and
wherein n is an integer from 1 to 4.

10. A mixture comprising more than one of the compounds of claim 9; wherein the compounds have more than one value for m, n, or both m and n.

11. The compound of claim 9, wherein m is 5.
12. The compound of claim 9, wherein m is from 6 to 17.
13. The compound of claim 9, wherein n is from 1 to 3.
14. The compound of claim 13, wherein m is 5.
15. The compound of claim 9, wherein n is 3.
16. The compound of claim 13, wherein m is 5.
17. The compound of claim 9, wherein n is 4.
18. The compound of claim 15, wherein m is 5.

* * * * *